US00PP35361P2

(12) United States Plant Patent
Danziger

(10) Patent No.: US PP35,361 P2
(45) Date of Patent: Aug. 29, 2023

(54) ***PORTULACA* PLANT NAMED 'DPOPAZNFUI'**

(50) Latin Name: *Portulaca oleracea*
Varietal Denomination: DPOPAZNFUI

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm

( * ) Notice: Subject to any disclaimer, the term of this patent is extended or adjusted under 35 U.S.C. 154(b) by 0 days.

(21) Appl. No.: 18/075,238

(22) Filed: Dec. 5, 2022

(51) Int. Cl.
*A01H 5/02* (2018.01)
*A01H 6/30* (2018.01)

(52) U.S. Cl.
USPC ..... Plt./471
CPC ..... *A01H 6/30* (2018.05)

(58) Field of Classification Search
USPC ..... Plt./471
CPC ..... A01H 6/30; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Portulaca* plant named 'DPOPAZNFUI' is disclosed, characterized by large, bright fuchsia flowers, an early, long blooming period, and a semi-upright, mounded, compact habit. The new variety is a *Portulaca*, typically produced as an ornamental plant.

2 Drawing Sheets

Figure 1:
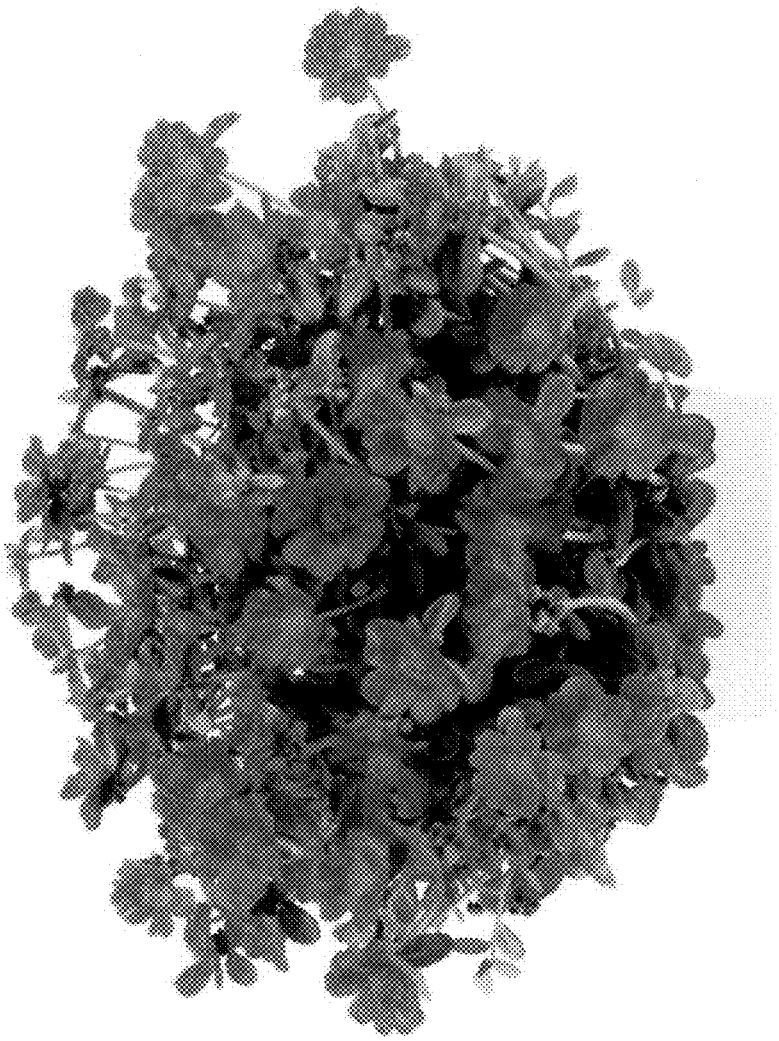

Latin name of the genus and species: *Portulaca oleracea.*
Variety denomination: 'DPOPAZNFUI'.

BACKGROUND OF THE INVENTION

The new *Portulaca* cultivar is a product of a planned breeding program conducted by the inventor, Gavriel Danziger in Moshav Mishmar Hashiva, Israel. The objective of the breeding program was to produce useful new *Portulaca* varieties for ornamental horticultural production. The crossing resulting in this new variety was made during August of 2015.

The seed parent is the unpatented, propriety variety referred to as *Portulaca* 'PT-14-1136'. The pollen parent is unidentified. The new variety was discovered in July of 2016 by the inventor in a group of seedlings resulting from the 2015 open-pollination, in a greenhouse in Moshav Mishmar Hashiva, Israel. After selection of the new variety, extensive confidential testing has been performed to determine and define the desirable characteristics of the new variety.

Asexual propagation of *Portulaca* was performed by vegetative basal cuttings in July of 2016, at the same nursery in Moshav Mishmar Hashiva, Israel. Date of first sale was Jan. 23, 2022, in Italy. This sale was made directly by the inventor or one who obtained the claimed invention directly or indirectly from the inventor. This sale and all public disclosures made between Jan. 23, 2022 and the filing of this application fall within the exception allowed under 102(b)(1).

SUMMARY OF THE INVENTION

The cultivar 'DPOPAZNFUI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPOPAZNFUI'. These characteristics in combination distinguish 'DPOPAZNFUI' as a new and distinct *Portulaca* cultivar:

1. Semi-upright, mounded, compact habit.
2. Large, bright fuchsia flowers.
3. Long blooming period, from spring to autumn.
4. Early flowering.
5. Freely branching habit.

PARENT COMPARISON

Plants of 'DPOPAZNFUI' are similar in some horticultural characteristics to the seed parent. The new variety, however, differs in the following:

1. The new variety has a more compact plant habit than the seed parent.
2. Flowers of the new variety are larger than flowers of the seed parent.
3. The new variety produces more flowers than the seed parent.

COMMERCIAL COMPARISONS

Plants of 'DPOPAZNFUI' are similar in some horticultural characteristics to the variety *Portulaca* 'DPAZFCHSIA', U.S. Plant Pat. No. 27,540P3. The new variety, however, differs in the following:

1. The new variety has a compact, semi-upright habit, while this comparator has a semi-trailing, slightly spreading habit.
2. Plants of the new variety are more dense than plants of this comparator.
3. Flowers of the new variety are larger than flowers of this comparator.
4. Foliage of the new variety is darker and wider than foliage of this comparator.

Plants of 'DPOPAZNFUI' are similar in some horticultural characteristics to the variety *Portulaca* 'DPORPZNAPR', unpatented. The new variety, however, differs in the following:

1. Plants of the new variety are more dense than plants of this comparator.
2. Flower color of the new variety is a bright fuchsia, while the flower color of this comparator is darker fuchsia.
3. Foliage of the new variety is wider than foliage of this comparator.

BRIEF DESCRIPTION OF THE PHOTOGRAPHS

The accompanying photograph in FIG. 1 illustrates in full color a typical plant of 'DPOPAZNFUI' at about 4 weeks of age, grown in a 12 cm pot.

Figure 2:
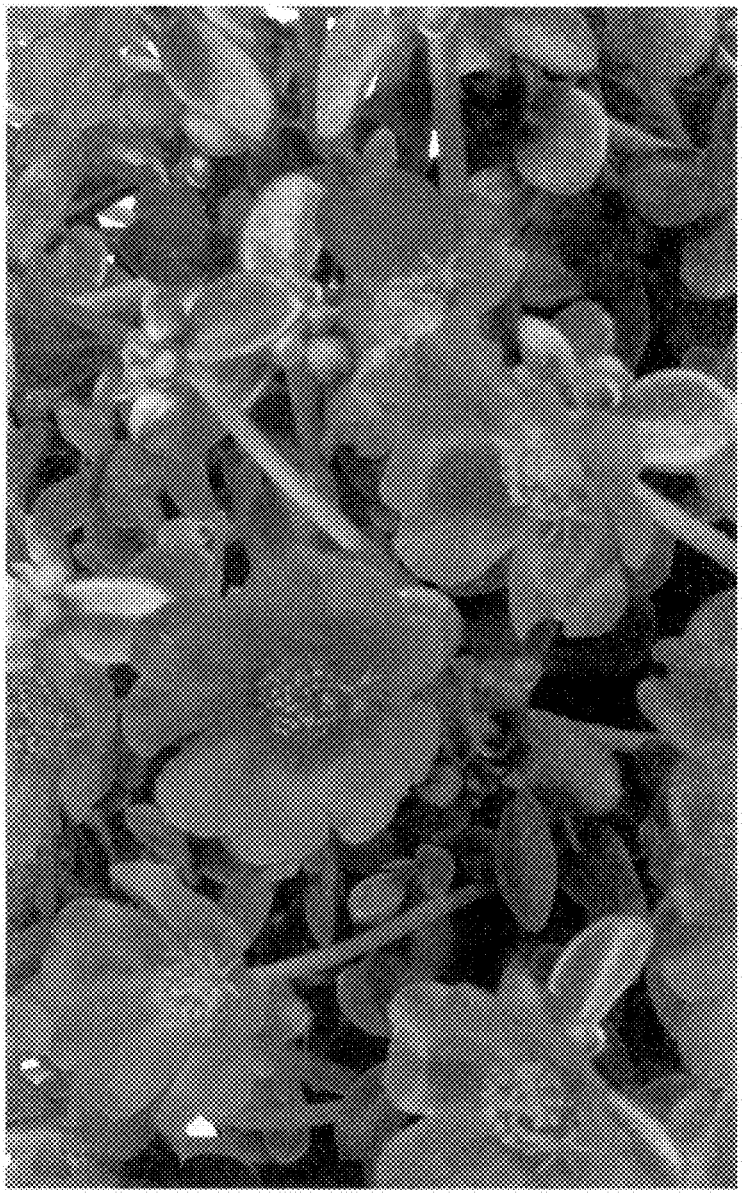

FIG. 2 illustrates a close-up view of typical flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPOPAZNFUI' plants grown outdoors in Moshav Mishmar Hashiva, Israel, under natural lighting. Measurements were taken during summer. The growing temperature ranged from approximately 24° C. to 36° C. during the days, 12° C. to 26° C. during the nights. Measurements and numerical values represent averages of typical plant types.

Botanical classification: *Portulaca oleracea* 'DPOPAZNFUI'.

PROPAGATION

Time to initiate rooting: 10 to 14 days at approximately 20° C.

Age of plant described: 4 weeks from a rooted cutting.

Root description: Fine, fibrous; close to RHS Yellow-White 158B in color, freely branching.

PLANT

Growth habit: Mounded, compact, dense.
Pot size of plant described: 12 cm.
Height: About 18 cm.
Plant spread: About 17 cm radius.
Growth rate: Medium.
Branching characteristics:
Length of lateral branches: 19 cm.
Diameter of lateral branches: 0.5 cm.
Quantity of lateral branches: About 8 to 10 per main stem.
Characteristics of primary lateral branches:
- *Diameter*.—About 0.3 to 0.4 cm.
- *Texture*.—Smooth.
- *Strength*.—Moderately strong.

Internode length: Close to the base: 1.5-2 cm; close to the tip: 0.7 cm.

FOLIAGE

Leaf:
- *Arrangement*.—Opposite to alternate, simple.
- *Quantity*.—Approximately 15 per branch.
- *Average length*.—Young: 1.5 cm; mature: 4.2 cm.
- *Average width*.—Young: 1 cm; mature: 2 to 2.7 cm.
- *Pubescence*.—Glabrous, succulent.
- *Shape*.—Obovate, spatulate.
- *Apex*.—Blunt (truncate).
- *Base*.—Cuneate.
- *Margin*.—Entire.
- *Texture*.—Smooth.
- *Aspect*.—45-80°.
- *Color*.—Upper side: Near RHS Green 137B. Under side: Near RHS Green 138B.
- *Venation*.—Indistinguishable from leaf blade.

Petiole:
- *Length*.—About 1.5 mm.
- *Diameter*.—About 1.8 mm.
- *Color*.—Near RHS Yellow-Green 144A.
- *Texture*.—Smooth, glabrous.

FLOWER

Natural flowering season: Spring to autumn.
Days to flowering from rooted cutting: About 4 weeks to the first flowers.
Inflorescence and flower type and habit: Single flower, freely flowering.
Rate of flower opening: About 3 days from bud to fully opened flower.
Flower longevity on plant: About 1 to 2 days.
Persistent or self-cleaning: Self-cleaning.

Bud:
- *Shape*.—Ovoid.
- *Length*.—1 to 1.2 cm.
- *Diameter*.—0.6 cm.
- *Color*.—Near RHS Yellow-Green 144B.

Flower size:
- *Diameter*.—About 4.7 cm.
- *Depth*.—About 2.9 cm.

Corolla/petals:
- *Arrangement*.—5 petals merged/fused at the base.
- *Length*.—2.3 cm.
- *Width*.—1.9 cm.
- *Quantity*.—5 petals.
- *Texture*.—Smooth, glabrous.
- *Apex*.—Emarginate, retuse.
- *Shape*.—Obovate with a cuneate base.
- *Margin*.—Entire.
- *Aspect*.—Mostly upright.
- *Color*.—When Opening, Upper Surface: RHS Purple-Red N67A. When Opening, Lower Surface: RHS Purple-Red N67B. Fully Opened, Upper Surface: RHS Purple-Red N66A Fully Opened, Lower Surface: RHS Purple-Red N66B.

Calyx/sepals:
- *Quantity per flower*.—2 per flower.
- *Shape*.—Fused into a tubular calyx. Pointed apex.
- *Length*.—1 cm.
- *Width*.—0.7 cm.
- *Apex*.—Acute.

*Base*.—Fused.

*Margin*.—Entire.

*Texture*.—Glabrous.

*Color*.—Upper Surface: Near RHS Yellow-Green 144B. Lower Surface: Near RHS Yellow-Green 144C.

Peduncles: None.

Fragrance: None.

REPRODUCTIVE ORGANS

Androecium:

Stamens:

*Number*.—Many, about 55.

*Filament length*.—Approximately 0.5 to 0.7 cm.

Anthers:

*Shape*.—Ovate.

*Length*.—Less than 0.5 mm.

*Color*.—Near RHS Yellow-Orange 14A.

*Pollen*.—Color: RHS Yellow-Orange 17A. Quantity: Abundant.

Gynoecium:

Pistil:

*Number*.—1.

*Length*.—1 cm.

*Style*.—Length: 0.89 cm. Color: Near RHS Yellow 13A.

*Stigma*.—Shape: Six branched stigma. Color: Near RHS Red-Purple 61B; Yellow 3B near base. Ovary Color: Near RHS Yellow-Green 144B.

OTHER CHARACTERISTICS

Seeds and fruits: Seeds are dark grey with a circular shape.

Disease/pest resistance: Neither resistance nor susceptibility observed. *Portulaca* is not typically susceptible to many diseases and pests. The most common diseases being typical root rots from over watering, or black stem, *Dichotomophthora portulaca*. The most common pest of *Portulaca* is Aphid.

Temperature tolerance: Will not tolerate temperatures below 7° C. High temperature tolerance near 40° C.

What is claimed is:

1. A new and distinct cultivar of *Portulaca* plant named 'DPOPAZNFUI' as herein illustrated and described.

* * * * *